United States Patent [19]

Pfeiffer et al.

[11] Patent Number: 4,547,357
[45] Date of Patent: Oct. 15, 1985

[54] N-HYDROXYETHYLATED 2,4,6-TRIIODOAMINOISOPHTHALIC ACID BISTRIHYDROXYBUTYLAMIDES, THEIR PREPARATION AND X-RAY CONTRAST MEDIA CONTAINING THEM

[75] Inventors: Heinrich Pfeiffer; Wolfgang Muetzel; Ulrich Speck, all of Berlin, Fed. Rep. of Germany

[73] Assignee: Schering, Aktiengesellschaft, Berlin and Bergkamen, Fed. Rep. of Germany

[21] Appl. No.: 451,374

[22] Filed: Dec. 20, 1982

[30] Foreign Application Priority Data

Dec. 18, 1981 [DE] Fed. Rep. of Germany ........ 3150916

[51] Int. Cl.[4] .................... C07C 103/78; A61K 49/04
[52] U.S. Cl. .......................................... 424/5; 564/153
[58] Field of Search ............................ 424/5; 564/153

[56] References Cited

U.S. PATENT DOCUMENTS

| | | | |
|---|---|---|---|
| 3,701,771 | 10/1972 | Almen et al. | 424/5 |
| 4,001,323 | 1/1977 | Felder et al. | 424/5 |
| 4,021,481 | 5/1977 | Almen et al. | 424/5 |
| 4,069,250 | 1/1978 | Wiegert | 424/5 |
| 4,250,113 | 2/1981 | Nordal et al. | 424/5 |
| 4,341,756 | 7/1982 | Sovak et al. | 424/5 |
| 4,352,788 | 10/1982 | Felder et al. | 424/5 |
| 4,364,921 | 12/1982 | Speck et al. | 424/5 |
| 4,396,597 | 8/1983 | Rakli et al. | 424/5 |
| 4,396,598 | 8/1983 | Lin | 424/5 |

FOREIGN PATENT DOCUMENTS 0033426 8/1981 European Pat. Off. .
1548594 7/1979 United Kingdom .

OTHER PUBLICATIONS

Jacobsen, Farmakoterapi, 3, 1982.

Primary Examiner—Thomas A. Waltz
Attorney, Agent, or Firm—Millen & White

[57] ABSTRACT

Novel N-hydroxyethylated 2,4,6-triiodoaminoisophthalic acid bistrihydroxybutylamides of Formula (I)

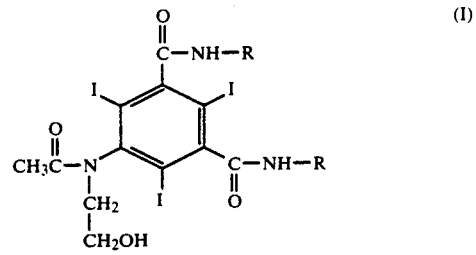

wherein R is a trihydroxybutyl residue, are excellently suitable, due inter alia, to their outstanding compatibility and high water solubility, as opacifying compounds in X-ray contrast media for use in X-ray diagnostic examination methods.

18 Claims, No Drawings

N-HYDROXYETHYLATED 2,4,6-TRIIODOAMINOISOPHTHALIC ACID BISTRIHYDROXYBUTYLAMIDES, THEIR PREPARATION AND X-RAY CONTRAST MEDIA CONTAINING THEM

BACKGROUND OF THE INVENTION

This invention relates to new X-ray contrast agents.

Iodine-containing, water-soluble X-ray contrast media are utilized for urography, angiography, myelography, gastrography, computerized tomography, and digital radiography. Additionally, there are other body cavities whose imaging is desired, such as, for example, the articular cavity, the bile duct, the bladder, and the pancreatic duct. It has been clearly apparent for some time that a single X-ray contrast medium cannot satisfy the requirements of such a large number of applications.

Use of the presently available X-ray contrast media is precluded for certain indications, or at least leaves much to be desired, for various reasons, e.g., due to inadequate compatibility in one or another respect, insufficient solubility, concentration, unsuitable pharmacokinetic properties, etc.

Substantial progress has been made with regard to the compatibility of these compounds by the development of nonionic X-ray contrast media in place of the heretofore known ionic contrast media. Special properties of these new media include low painfulness in angiography, small effects on the circulation, and small epileptogenic effect. The clinical experience gained in the meantime with nonionic and readily water-soluble X-ray contrast media (see, e.g., B. Hammer and W. Lackner: "Iopamidol, a New Non-Ionic Hydrosoluble Contrast Medium for Neuroradiology"; Neuroradiology 19:119-121, 1980) showed, on the other hand, that even the most recent opacifying compounds, among which are, for example, iopamidol, metrizamide, and iohexol, still are not devoid of side effects.

SUMMARY OF THE INVENTION

Therefore, it is an object of this invention to provide new non-ionic X-ray contrast media possessing, in addition to the required physicochemical characteristics, such as, above all, good water solubility and stability under sterilization conditions, a further improved neural compatibility, and, as well to overcome or ameliorate the mentioned disadvantages.

Upon further study of the specification and appended claims, further objects and advantages of this invention will become apparent to those skilled in the art.

These objects have been attained by this invention by providing novel N-hydroxyethylated 2,4,6-triiodoaminoisophthalic acid bistrihydroxybutylamides of Formula (I)

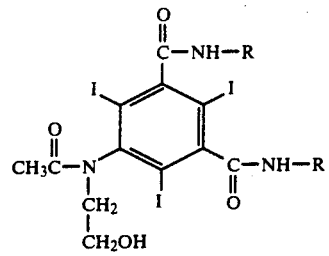

wherein R is trihydroxybutyl.

DETAILED DESCRIPTION

Suitable trihydroxybutyl groups as R include all isomers and enantiomers of any butyl group, i.e., containing 4 carbon atoms, such as, for example, the 2,3,4-trihydroxybutyl groups, 1,1,1-trishydroxymethylmethyl, the erythro and threo forms of 1,3,4-trihydroxybutyl, etc.

By structural modification of conventional contrast medium compounds from DOS No. 2,726,196, (or U.S. Pat. No. 4,250,113), surprisingly, it has been possible to provide novel triiodinated 5-aminoisophthalic acid bisamides having superior neural compatibility, and which exhibit additional advantages with respect to numerous properties critical for utilization of X-ray contrast media. Especially important is the reduction in the undesirable lipophilic properties of the novel contrast media, obtained by voluminous, extremely hydrophilic substituents. Such a reduction in lipophilicity enables an extremely good general compatibility manifesting itself in a higher $LD_{50}$ upon i.v. injection in animals, and in a diminished frequency of nausea and allergy-like reactions in clinical usage.

Further surprising and advantageous is the fact that the introduction of voluminous substituents in the triiodo aromatic of Formula (I) does not result in a rise in viscosity. This would have made the utilization of the compounds of this invention very problematic.

In Table I, the following compounds are compared with respect to neural and general compatibility:

$A_1$ = 5-[N-(2-Hydroxyethyl)acetylamino]-2,4,6-triiodoisophthalic acid bis(threo-1,3,4-trihydroxybut-2-yl)diamide $A_2$ = 5-[N-(2-Hydroxyethyl)acetylamino]-2,4,6-triiodoisophthalic acid bis(erythro-1,3,4-trihydroxybut-2-yl)diamide B = Metrizamide (DOS No. 2,031,724 or U.S. Pat. No. 3,701,771)

C = Iopamidol (DOS No. 2,547,789 or U.S. Pat. No. 4,001,323)

D = Iohexol (DOS No. 2,726,196 or U.S. Pat. No. 4,250,113)

TABLE I

| Compound | $A_1$ | $A_2$ | B | C | D |
|---|---|---|---|---|---|
| Neural compatibility | | | | | |
| Rat, pericerebral $ED_{50}$ mg I/kg | 171 (122–207) | 188 (142–265) | 62 (54–72) | 154 (123–216) | 83 (60–123) |
| Rat, intracisternal $ED_{50}$ mg I/kg | 130 | 130 | 48 (39–61) | 116 (95–157) | 67 (58–88) |
| General compatibility Mouse $LD_{50}$ (g I/kg) | 17 | 22 | 14 | 15 | 15 |
| Iodine content (%) | 45 | 45 | 48 | 49 | 46 |
| Number of hydroxy groups/molecule | 7 | 7 | 4 | 5 | 6 |
| Viscosity (mPa · s) 37° C. | 5.8 | 6.2 | 6.2 | 4.5 | 5.5 |

TABLE I-continued

| Compound | A₁ | A₂ | B | C | D |
|---|---|---|---|---|---|
| 300 mg I/ml | | | | | |

It can be seen from the data of Table I that compounds A₁ and A₂ are superior to the comparison compounds with respect to neural as well as general compatibility.

The compounds of this invention can be conventionally sterilized in a suitable preparation by heating to 120° C. The low viscosity of these solutions permits rapid injection.

Because of their good pharmacological properties, the novel compounds of Formula (I) are excellently suitable as opacifying compounds in all fields of application of water-soluble X-ray contrast media for intravenous administration, especially for angiography, urography, myelography, and computerized tomography. Since the novel X-ray contrast media are not absorbed, they are also suitable for oral administration, for example to visualize the gastrointestinal tract.

Consequently, the invention also relates to novel X-ray contrast media based on compounds of Formula (I).

The novel X-ray contrast media based on the compounds of this invention can be produced conventionally, for example by bringing the opacifying compound into a form suitable for intravenous administration together with the additives customary in galenic pharmacy, e.g., stabilizers, such as sodium edetate, calcium disodium edetate, physiologically acceptable buffers, and the like. The concentration of the novel X-ray contrast media in the aqueous medium is dependent on the conventional requirements of the method of X-ray diagnostics employed. The preferred concentrations of the novel compounds usually range from 50 to 400 mg I/ml and the preferred unit dosages are usually from 2 to 500 ml. Concentrations of 100 to 400 mg I/ml are especially preferred. Unless specified otherwise herein, the use and administration of the X-ray contrast media of this invention is fully conventional and analogous, e.g., to that of the conventional X-ray contrast agent, metrizamide, Iopamidol, Diatrizoate, Iohexol.

The present invention furthermore concerns a process for the preparation of compounds of Formula (I), comprising conventionally N-alkylating a compound of Formula (II) in the 5-position

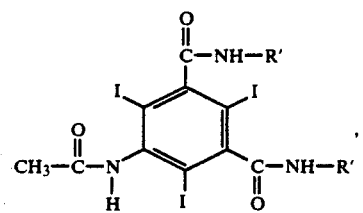

(II)

wherein R' is the same as R defined above, but free hydroxy groups present in the molecule can be in the blocked form, using a compound of Formula III

(III)

wherein

A and B combined represent the oxygen atom of an oxido ring, or

B is an hydroxy group and

A is a chlorine, sulfate or $C_{1-2}$-alkyl sulfate, phenyl or tosyl sulfate, and, optionally, subsequently liberating blocked hydroxy groups.

The N-alkylation of the 5-acylamino group according to this invention is conducted by means of methods known to those skilled in the art. Thus, the compounds of Formula (II) can be reacted, for example, in a suitable solvent, such as methanol, ethanol, or 1,2-propanediol in the presence of an alkali metal alcoholate or alkali metal amide with the compound of Formula (III), for example with chloroethanol or ethylene oxide, at a temperature of from room temperature to 80° C., preferably 20°-60° C.

The alkylation can also be conducted by using the compound II with intermediarily blocked hydroxy groups. In this case, the conventional blocking of the hydroxy groups in the form of a ketal, acetal, ortho ester, or triphenylmethyl ether either has taken place as early as during the production of the preliminary products, or is effected only prior to the reaction of this invention. This step takes place according to customary methods by the introduction of groups which can be readily split off, for example by etherification (e.g., introduction of the triphenylmethyl ether). The blocking of the hydroxy groups can also be achieved by ketalization or acetalization, for example with acetaldehyde, acetone, or dihydropyran.

The subsequent cleavage of the intermediarily introduced blocking groups, with liberation of the ultimately desired hydroxy groups, likewise takes place according to methods generally known to those skilled in the art. Thus, the cleavage of the blocking groups can be effected without a separate reaction stage together with the working up and isolation of the reaction products. However, such cleavage can also be accomplished in the usual way in a separate reaction step. Acyl blocking groups can be split off, for example, by alkaline hydrolysis, and acetal, ketal, or ether blocking groups by acidic hydrolysis.

The starting compounds of Formula (II) are, in part, known, such as, for example 5-acetylamino-2,4,6-triiodoisophthalic acid bis(threo-1,3,4-trihydroxybut-2-yl)diamide (European patent application No. 0,033,426), or they can be prepared pursuant to methods known to persons skilled in the art. The starting material is the conventional 5-acetylamino-2,4,6-triiodoisophthalic acid dichloride (see U.S. Pat. Nos. 3,701,771 and 4,021,481 (Compound No. 11 of Table 4 and 5) and European application No. 0,033,426, whose entire disclosure is incorporated by reference herein). Dissolved in a suitable aprotic solvent, such as dimethylacetamide for example, it can be reacted with the desired aminobutanetriol of Formula (IV)

R'-NH₂          (IV)

wherein

R' has the same meaning as defined for R, but several of the hydroxy groups can be present in the blocked form.

The aminobutanetriols of Formula (IV) necessary for the above-described reaction are, in part, known, such as, for example, 1,1,1-trishydroxymethylmethylamine, D,L-erythro-2-amino-1,3,4-trihydroxybutane, cis-2,2-dimethyl-6-hydroxy-5-amino-1,3-dioxepane, or they can be prepared according to methods known to those skilled in the art, such as, for example, analogously to the preparation of 2-amino-1-(2,2-dimethyl-1,3-dioxolan-4-yl)ethanol, which can be obtained as follows. (In this regard, see commonly assigned U.S. application Ser. No. 451,375 of Dec. 20, 1982 filed on even date, whose entire disclosure is incorporated by reference herein.)

2-Amino-1-(2,2-dimethyl-1,3-dioxolan-4-yl)ethanol (1) 3-Chloro-1,2,4-butanetriol Prepared according to the directions by W. Reppe et al., Liebigs Ann. Chem. 596 : 137 (1955).

Yield: 272 g (97% of theory)

$C_4H_9ClO_3$ (140.568): Calculated: 34.18% C, 6.45% H, 25.22% Cl; Found: 34.07% C, 6.58% H, 25.07% Cl.

(2) 2-Chloro-2-(2,2-dimethyl-1,3-dioxolan-4-yl)-ethanol 258 ml of 2,2-dimethoxypropane is added dropwise within 2 hours to an agitated and water-cooled solution of 272 g of 3-chloro-1,2,4-butanetriol and 0.5 ml of concen-trated sulfuric acid in one liter of acetone. The reaction is completed after another 4 hours. The solution is neutralized by adding 3.8 g of barium hydroxide. The mixture is stirred for another 30 minutes, filtered off from the solid matter, and evaporated to dryness under vacuum, producing 2-chloro-2-(2,2-dimethyl-1,3-dioxolan-4-yl)ethanol as a yellow oil.

Yield: 340 g (94% of theory).

(3) 2-(2,2-Dimethyl-1,3-dioxolan-4-yl)ethylene Oxide:

340 g of 2-chloro-2-(2,2-dimethyl-1,3-dioxolan-4-yl)e-thanol is dissolved in 1.5 l of absolute ether. At 5° C., 130 g of pulverized potassium hydroxide in total is added within 30 minutes under intensive agitation, the temperature being maintained at between 5° and 15° C. by cooling. The refrigerating bath is then exchanged for a water bath (40° C.), and the suspension is heated for 2 hours under gentle refluxing. After heater and cooler have been turned off, the phases begin to separate. After standing overnight, the mixture is vacuum-filtered over kieselguhr/sand. The residue is extracted with ether. The combined ether solutions are concentrated over a 60 cm Vigreux column. The residue (260 g) is distilled under vacuum, thus obtaining 180 g of a colorless liquid, which is fractionated, yielding 2-(2,2-dimethyl-1,3-diox-olan-4-yl)ethylene oxide at 65° C./13 mm. Yield: 154.3 g (57% of theory).

As a by-product, 10.8 g (4% of theory) of 4,4-dimeth-yl-3,5,8-trioxabicyclo[5.1.0]octane is obtained ($bp_{13}$:81° C.).

(4) 2-Amino-1-(2,2-dimethyl-1,3-dioxolan-4-yl)-ethanol

A solution of 73.4 g of 2-(2,2-dimethyl-1,3-dioxolan-4-yl)ethylene oxide in 400 ml of 25% strength ammonia is heated in an autoclave for 4 hours to 130° C. The slightly yellowish solution is concentrated to dryness under vacuum; during this step, the residue crystallizes. 2-Amino-1-(2,2-dimethyl-1,3-dioxolan-4-yl)ethanol is re-crystallized from ethanol/ether, mp 94°-96° C.

Yield: 52.8 g (64.2% of theory).

The starting compounds of Formula (II) can be prepared according to the following general method:

Within 15 minutes, a solution of 51 g (80 mmol) of 5-acetylamino-2,4,6-triiodoisophthalic acid dichloride (DOS No. 2,031,724) in 100 ml of dimethylacetamide is added dropwise under slight cooling and agitation at room temperature to a solution or suspension of 180 mmol of free or blocked aminobutanetriol of general Formula IV in 100 ml of dimethyl-acetamide. Then 25.1 ml (180 mmol) of triethylamine is added dropwise. After agitation overnight, the suspension is heated for 4 hours to 50° C., thereafter cooled and acidified with 4.5 ml of aqueous concentrated hydrochloric acid. After several hours, the thus-precipitated triethylamine hydrochloride (about 22 g, 90% of theory) is vacuum filtered, and the filtrate is extensively concentrated under vacuum. The product is combined with 200 ml of water and 4 ml of aqueous concentrated sodium hydroxide solution (pH about 10) and stirred for several hours. During this aqueous-acidic and aqueous alkaline treatment, any blocking groups present in the amide residues are generally split off quantitatively. Otherwise, more vigorous conditions must be chosen, or other customary splitting-off methods must be employed. If the bisamide of general Formula II is not precipitated from the aqueous solution, the latter is treated with a cation ex-changer and optionally with an anion exchanger. For purposes of additional purification, the isolated product can also be boiled with ethanol.

The following compounds are obtained according to the foregoing general procedure:

(1) 5-Acetylamino-2,4,6-triiodoisophthalic Acid Bis(threo-1,3,4-trihydroxybut-2-yl)diamide Yield: 51.8 g (80.4% of theory); mp 258°-260° C. (decomposition). In accordance with EP 0,033,426: mp 246°-247° C. and yield 55% of theory.

(2) 5-Acetylamino-2,4,6-triiodoisophthalic Acid Bis(erythro-1,3,4-trihydroxybut-2-yl)diamide Yield: 39 g (61% of theory); mp 275°-276° C. (decomposition), using 180 mmol of D,L-erythro-2-amino-1,3,4-trihydroxybutane [Kiss et al., Helv. Chim. Acta 37 : 1471 (1954)]or 180 mmol of cis-2,2-dimethyl-6-hydroxy-5-amino-1,3-dioxepane (R. Ranganathan, M. Sovak, Abstracts of Papers, 182nd ACS National Meeting 1981).

(3) 5-Acetylamino-2,4,6-triiodoisophthalic Acid Bis(2,3,4-trihydroxybut-1-yl)diamide Yield: 47.8 g (74% of theory); mp 279°-283° C. (decomposition), using 180 mmol of 2-amino-1-(2,2-dimethyl-1,3-dioxolan-4-yl)ethanol.

(4) 5-Acetylamino-2,4,6-triiodoisophthalic Acid Bis(1,1,1-trishydroxymethylmethyl)diamide Yield: 23.5 g (36.4% of theory); mp 166°-170° C. (decomposition), using 180 mmol of trishydroxymethyl-methyl-amine. In a deviation from the general directions, trishydroxymethylmethylamine is likewise used in place of triethylamine, and the reaction mixture is heated for 4 days to 50° C.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

5-[N-(2-Hydroxyethyl)acetylamino]-2,4,6-triiodoisophthalic Acid Bis(threo-1,3,4-trihydroxybut-2-yl)diamide A methylate solution from 100 ml of methanol and 2.48 g (108 mmol) of sodium is combined with 110 ml of 1,2-propylene glycol, 40.4 g (50 mmol) of 5-acetylamino-2,4,6-triiodoisophthalic acid bis(threo-1,3,4-trihydroxybut-2-yl)-diamide, and, for additional washing, with 50 ml of methanol. Under agitation and heating to 50° C., a solution is formed from which the methanol is distilled off under vacuum. The solution is then combined with 6.7 ml (100 mmol) of 2-chloroethanol and further stirred for 5 hours at 50° C. After cooling, the suspension is combined with one liter of acetone and filtered after one hour. The precipitate, which contains sodium chloride, is again extracted under agitation with acetone and vacuum-filtered. This mixture (about 47 g) is dissolved in 470 ml of water and passed over a column with 600 ml of action exchanger IR 120. The aqueous eluate is extensively concentrated under vacuum, the residue is taken up in 370 ml of water and treated analogously with the anion exchanger IRA 140 and worked up. Extraction of the residue by boiling with 165 ml of isopropanol yields 24.6 g (57.7% of theory) of the title compound, mp 250°–254° C. (decomposition).

Iodine, calculated 44.73%, found 44.1%.
100 ml of water dissolves more than 70 g.

EXAMPLE 2

5-[N-(2-Hydroxyethyl)acetylamino]-2,4,6-triiodoisophthalic Acid Bis(erythro-1,3,4-trihydroxybut-2-yl)diamide Analogously to Example 1, 40.3 g (50 mmol) of 5-acetylamino-2,4,6-triiodoisophthalic acid bis(erythro-1,3,4-trihydroxybut-2-yl)diamide is hydroxyethylated and worked up.

Yield after refluxing with isopropanol: 22.6 g (53.2% of theory) of title compound, mp 292°–296° C. (decomposition).

Iodine, calculated 44.73%, found 44.3%.
100 ml of water dissolves more than 70 g.

EXAMPLE 3

5-[N-(2-Hydroxyethyl)acetylamino]-2,4,6-triiodoisophthalic Acid Bis(1,1,1-trishydroxymethylmethyl)diamide Analogously to Example 1, 40.3 g (50 mmol) of 5-acetylamino-2,4,6-triiodoisophthalic acid bis(1,1,1-trishydroxymethylmethyl)diamide is hydroxyethylated and worked up.

Yield after refluxing with isopropanol: 23.7 g (56.9% of theory) of title compound, mp 212°–218° C. (decomposition).

Iodine, calculated 44.73%, found 44.2%.
100 ml of water dissolves more than 70 g.

EXAMPLE 4

5-[N-(2-Hydroxyethyl)acetylamino]-2,4,6-triiodoisophthalic Acid Bis(2,3,4-trihydroxybut-1-yl)-diamide Analogously to Example 1, 40.3 g (50 mmol) of 5-acetylamino-2,4,6-triiodoisophthalic acid bis(2,3,4-trihydroxybut-1-yl)diamide is hydroxyethylated and worked up.

Yield after refluxing with isopropanol: 27.6 g (64.7% of theory) of title compound, mp 283°–287° C. (decomposition).

Iodine, calculated 44.7%, found 44 2%.
100 ml of water dissolves more than 70 g.

EXAMPLE 5

Preparation of a Ready-for-Use Aqueous Solution Containing 320 mg Iodine/ml

| | |
|---|---|
| 5-[N—(2-Hydroxyethyl)acetylamino]-2,4,6-triiodoisophthalic acid bis(threo-1,3,4-trihydroxybut-2-yl)diamide | 71.5 g |
| Calcium disodium edetate | 0.01 g |
| 2-Amino-2-(hydroxymethyl)-1,3-propanediol | 0.12 g |
| 2N Hydrochloric acid to adjust to pH 7.1 | |
| Double-distilled water ad | 100 ml |

The solution is filled into ampoules or multivials and sterilized at 120° C.

EXAMPLE 6

Preparation of a Ready-for-Use Aqueous Solution Containing 380 mg Iodine/ml

| | |
|---|---|
| 5-[N—(2-Hydroxyethyl)acetylamino]-2,4,6-triiodoisophthalic acid bis(erythro-1,3,4-trihydroxybut-2-yl)diamide | 85.1 g |
| 2-Amino-2-(hydroxymethyl)-1,3-propanediol | 0.12 g |
| Calcium disodium edetate | 0.01 g |
| 2N Hydrochloric acid to adjust to pH 7.1 | |
| Double-distilled water ad | 100 ml |

The solution is filled into ampoules or multivials and sterilized at 120° C.

EXAMPLE 7

Preparation of a Ready-for-Use Aqueous Formulation for Gastrography, Iodine Content 380 mg I/ml

| | |
|---|---|
| 5-[N—(2-Hydroxyethyl)acetylamino]-2,4,6-triiodoisophthalic acid bis(1,1,1-trishydroxymethylmethyl)diamide | 85.1 g |
| Calcium disodium edetate | 0.01 g |
| Anise oil | 0.14 g |
| Polyoxyethylene sorbitan oleate | 0.75 g |
| Double-distilled water ad | 100 ml |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An N-hydroxyethylated 2,4,6-triiodoaminoisophthalic acid bistrihydroxybutylamide of the formula

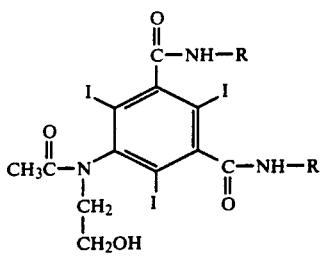

wherein R is trihydroxybutyl with the exception of 1,1,1-trishydroxymethylmethyl.

2. 5-[N-(2-hydroxyethyl)acetylamino]-2,4,6-triiodoisophthalic acid bis(threo-1,3,4-trihydroxybut-2-yl)diamide, a compound of claim 1.

3. 5-[N-(2-hydroxyethyl)acetylamino]-2,4,6-triiodoisophthalic acid bis(erythro-1,3,4-trihydroxybut-2-yl)diamide, a compound of claim 1.

4. 5-[N-(2-hydroxyethyl)acetylamino]-2,4,6-triiodoisophthalic acid bis(2,3,4-trihydroxybut-1-yl)-diamide, a compound of claim 1.

5. An X-ray contrast agent comprising an amount of opacifying compound of claim 1 effective as an X-ray contrast agent and a pharmaceutically acceptable carrier.

6. An agent of claim 5 wherein the concentration of opacifying agent is 50–400 mg I/ml.

7. An agent of claim 6 wherein the concentration of opacifying agent is 100–400 mg I/ml.

8. An X-ray contrast agent of claim 5 in a unit dosage form having a volume of 2–500 ml.

9. An X-ray contrast agent of claim 6 in a unit dosage form having a volume of 2–500 ml.

10. An X-ray contrast agent of claim 7 in a unit dosage form having a volume of 2–500 ml.

11. A method of opacifying a desired body cavity of a patient with respect to X-rays, comprising administering to the patient an amount of an agent of claim 5 effective to opacify the desired body cavity.

12. A method of visualizing a body cavity of a patient by X-ray diagnosis, comprising administering to the patient an amount of an agent of claim 5 effective to opacify the desired body cavity, then irradiating the body cavity with X-rays and detecting the X-rays passing through the patient.

13. A method of claim 12 wherein the method is angiography.

14. A method of claim 12 wherein the method is urography.

15. A method of claim 12 wherein the method is myelography.

16. A method of claim 12 wherein the method is computerized tomography.

17. A method of visualizing a body cavity of a patient by X-ray diagnosis, comprising administering to the patient an amount of an agent of claim 6 effective to opacify the desired body cavity, then irradiating the body cavity with X-rays and detecting the X-rays passing through the patient.

18. A method of visualizing a body cavity of a patient by X-ray diagnosis, comprising administering to the patient an amount of an agent of claim 8 effective to opacify the desired body cavity, then irradiating the body cavity with X-rays and detecting the X-rays passing through the patient.